United States Patent [19]

Stoddard

[11] Patent Number: 5,545,833
[45] Date of Patent: Aug. 13, 1996

[54] PHOSPHORUS-CONTAINING POLYMERS AND FIBERS FORMED THEREFROM

[75] Inventor: John W. Stoddard, Gulf Breeze, Fla.

[73] Assignee: Monsanto Company, St. Louis, Mo.

[21] Appl. No.: 453,938

[22] Filed: May 30, 1995

[51] Int. Cl.⁶ ............................ C08G 69/42; B32B 27/34
[52] U.S. Cl. ..................... 528/337; 528/313; 528/319; 528/322; 528/335; 528/336; 528/347; 428/395; 428/364
[58] Field of Search .................................. 528/322, 347, 528/335, 313, 319, 336, 337; 428/395, 364

[56] References Cited

U.S. PATENT DOCUMENTS

| | | | |
|---|---|---|---|
| 2,646,420 | 7/1953 | Morgan | 528/337 |
| 3,108,991 | 10/1963 | Pellon et al. | 528/337 |
| 3,142,662 | 7/1964 | Huffman | 528/313 |
| 3,542,743 | 11/1970 | Flamand | 528/335 |
| 3,658,634 | 4/1972 | Yanagi et al. | 524/145 |
| 4,092,302 | 5/1978 | Pickett, Jr. et al. | 528/337 |
| 4,579,762 | 4/1986 | Ucci | 428/95 |
| 4,701,518 | 10/1987 | Osborn et al. | 528/336 |
| 4,879,180 | 11/1989 | Blyth et al. | 428/395 |
| 5,108,684 | 4/1992 | Anton et al. | 264/176.1 |
| 5,369,160 | 11/1994 | Adyha et al. | 524/140 |

FOREIGN PATENT DOCUMENTS 1102009   12/1965   United Kingdom.

OTHER PUBLICATIONS

J. W. Stoddard, O. A. Pickett, C. J. Cicero and J. H. Saunders, Flame–Retarded Nylon Carpets, Textile Research Journal, vol. 45, No. 6, Jun. 1975, pp. 474–483.

M. Rauhut and H. Currier, Reactions of Bis(2–cyanoethyl)phosphine Oxide, Journal of Organic Chemistry, vol. 26 May, (1961) pp. 4628–4632.

*Primary Examiner*—James J. Seidleck
*Assistant Examiner*—P. Hampton-Hightower

[57] ABSTRACT

A polymer including as integral parts of polymer chain, amide groups of the formula

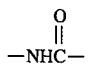

and phosphinic acid-salt groups of the formula

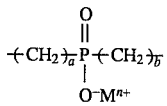

wherein a and b are both greater than or equal to 2 and M is selected from the group of metal cations where $n=1$ or $n=2$.

The polymer of the present invention is particularly useful in forming stain-resistant fibers for carpet pile.

20 Claims, No Drawings

PHOSPHORUS-CONTAINING POLYMERS AND FIBERS FORMED THEREFROM

BACKGROUND OF THE INVENTION

1. Field of the Invention

The present invention relates to phosphorus-containing polymers useful in fiber or resin manufacture. More preferably, the present invention is directed to polyamide polymers having phosphinic acid-salt groups in the polymer chain and which exhibit stain and flame resistance.

The term "fiber" as used herein is defined to include fibers of extreme or indefinite length (i.e., filaments) as well as fibers of short length (i.e., staple).

The term "yarn" as used herein is defined to be a continuous strand of fibers.

The term "polyamide" as used herein is defined to be a polymer whose repeating units are joined by amide linkages.

The term "polymer" as used herein is defined to encompass homopolymers, copolymers and the like, as well as polymer blends.

The term "resin" as used herein includes (but is not limited to) plastics used in molded or extruded parts.

2. Background of the Invention

Carpet with pile made from polyamide fibers has become a popular floor covering for both residential and commercial applications. Such carpet is relatively inexpensive and offers a desirable combination of qualities including durability, comfort, safety, warmth and aesthetic appearance. Polyamide fibers, for example fibers of polyhexamethylene adipamide (more commonly known as nylon 6,6) or polycaprolactam (more commonly known as nylon 6) are of specific value in this utility.

In many polyamide pile carpet manufacturing processes, the pile is dyed to a desired color with acid dyes, as many polyamides including nylon 6,6 and nylon 6 are very receptive to these dyes. This receptivity to acid dyes, however, can also manifest itself in a susceptibility to staining by natural or artificial acid dyes which typically exist in numerous consumer products such as foods and drinks.

One known method to impart stain resistance to nylon fibers includes topically applying to the fiber surface certain materials or compounds which function as stainblockers, such as those disclosed in U.S. Pat. No. 4,879,180 to Blyth et al. While this topical treatment successfully improves resistance to staining by acid dyes, the degree of stain resistance can decrease over time if the carpet is subjected to heavy use or harsh chemical cleaning.

Alternatively, it is known from, for example, U.S. Pat. No. 4,579,762 to Ucci, to form stain resistant fibers from nylon 6 or 6,6 polymer having a portion of the nylon-forming monomers replaced with a corresponding amount of an appropriate sulfonated aromatic monomer. Unfortunately, these polymers can exhibit undesirable foaming during polymerization.

Phosphorus-containing polyamides, as well as fibers and films formed therefrom, have been reported in the prior art. For example, U.S. Pat. No. 2,646,420 discloses high shrinkage fibers of polyamides containing recurring

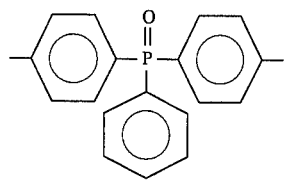

radicals joined by amide linkages while British Patent No. 1,102,009 discloses low melting polyamide films containing recurring

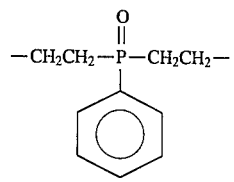

Also, U.S. Pat. No. 3,108,991 discloses water soluble, flame resistant homopolyamides containing, for example, recurring

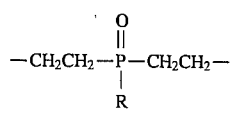

units, where R is a lower alkyl. Phosphorus-containing polyamides useful in certain applications are also disclosed in U.S. Pat. No. 4,092,302, assigned to the assignee of the present invention.

None of these phosphorus-containing polyamides are shown to exhibit any degree of resistance to staining by acid dyes.

A need therefore exists for a polymer which provides the beneficial characteristics of polyamides without the acid dye stain susceptibility that many polyamides exhibit.

SUMMARY OF THE INVENTION

The present invention satisfies these needs and achieves other benefits set forth in more detail below by providing a polymer including as integral parts of polymer chain, amide groups of the formula

and phosphinic acid-salt-groups of the formula

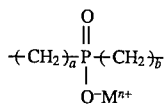

wherein a and b are both greater than or equal to 2 and $M^{n+}$ is selected from the group of cations where n=1 (preferably lithium, sodium or potassium) or n=2 (preferably magnesium).

The polymer of the present invention is particularly useful in forming stain-resistant fibers for carpet pile.

DETAILED DESCRIPTION OF THE PREFERRED EMBODIMENTS

The polymer of the present invention includes as an integral part of the polymer chain amide groups of the formula

and phosphinic acid-salt groups of the formula

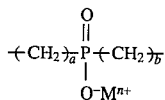

wherein a and b are both greater than or equal to 2 and $M^{n+}$ is selected from the group of cations wherein n=1 or n=2. In the embodiment where n=1, $M^{n+}$ is preferably a lithium ($Li^+$), sodium ($Na^+$) or potassium ($K^+$) ion, while in the embodiment where n=2, $M^{n+}$ is preferably a magnesium ion ($Mg^{2+}$). When n=2 (i.e., $M^{n+}=M^{2+}$), it will be understood by one of ordinary skill that $M^{2+}$ further bonds ionically with an additional neighboring oxygen anion from a phosphinic acid salt.

The polymer of the present invention preferably contains from about 0.1% to 5.0% by weight phosphorus based on the total weight of the polymer, most preferably from 0.1% to 1.0% by weight phosphorus based on the total weight of the polymer.

In a particularly preferred embodiment, the polymer is a polyamide as defined above, i.e., a polymer with repeat units joined by amide linkages

In this embodiment, therefore, the amide groups function as linkages between repeat units in the polyamide of the present invention.

Representative repeat units of the polyamide of the present invention include the following:

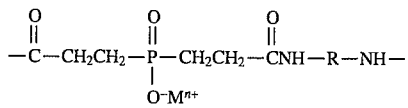

(I)

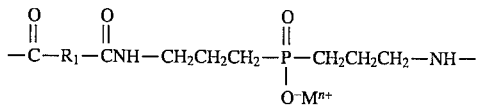

(II)

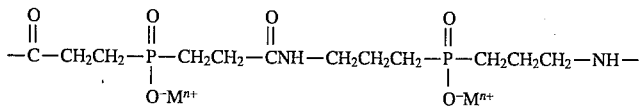

(III)

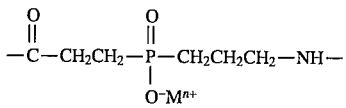

(IV)

wherein $M^{n+}$ is defined as above, n=1 or 2 and R and $R_1$ each represent an alkyl having 4 to 12 carbon atoms.

Polymers of this invention are preferably prepared by condensation of difunctional polyamide-forming reactants, e.g., diamines and dicarboxylic acids or an amide-forming derivative of dicarboxylic acids and/or lactams or aminocarboxylic acids or an amide-forming derivative of aminocarboxylic acid, by conventional techniques, such as by melt polymerization or solution polymerization. Generally, when one or more of the difunctional reactants is an aromatic diamine, such as para- or meta-phenylene diamine, the polymer is prepared according to conventional polyamide solution polymerization techniques by reaction of the diamine with the acid chloride of the dicarboxylic acid in an appropriate solvent (e.g., dimethylacetamide). Interfacial polymerization may also be used.

Preferred polymers of the invention may be conveniently prepared from dicarboxylic acids and aliphatic diamines by conventional melt polymerization in which an aqueous solution of at least one diamine-dicarboxylic acid salt is heated to remove water and effect polymerization. Each salt is conveniently prepared by simply mixing substantially equimolar amounts of a dicarboxylic acid and an aliphatic diamine in water. The salts then may be isolated from their respective solutions and combined in water to provide an aqueous solution of salts or the individual salt solutions may be combined.

In the process for producing the polyamide of the present invention, at least one of the diamine dicarboxylic acid salts in the above reaction must be a phosphorus-containing diamine-dicarboxylic acid salt to form the polymer of the present invention. Consequently, either a phosphorus-containing dicarboxylic acid or a phosphorus-containing diamine is utilized in forming the phosphorus-containing salt. Preferably, a phosphorus-containing dicarboxylic acid of the structure

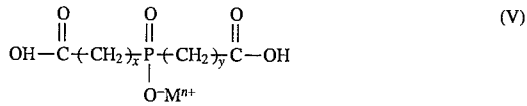 (V)

wherein $M^{n+}$ is selected from the group of cations where n=1 or n=2, and wherein x and y are each greater than or equal to 2, is reacted with an equimolar amount of a diamine of the formula

 (VI)

wherein $R_2$ represents a hydrocarbon radical having 4 to 12 carbon atoms, for example, polymethylene (e.g., hexamethylene), metaphenylene, paraphenylene, or the like.

Most preferably, the phosphorus-containing dicarboxylic acid salt has the structure:

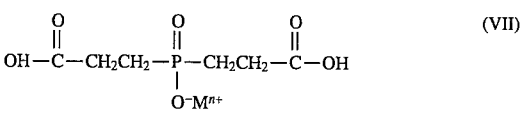 (VII)

where $M^{n+}$ is defined as above.

Suitable phosphorus-containing dicarboxylic acid salts may be formed from the oxidation and subsequent hydrolysis with suitable diamines of

 (VIII)

a compound previously available from Strem Chemicals, Inc., Newburyport, Mass., for the embodiment wherein x=2 and y=2. This oxidation and hydrolysis forms

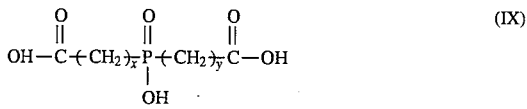 (IX)

which is preferably reacted with one equivalent of a metal hydroxide to form (VII). Suitable diamines of the formula (VI) are commercially available from Aldrich Chemicals, USA.

An alternate synthesis utilizes commercially available hypophosphorous acid (Aldrich) as starting material. This acid is first treated with trimethyl orthoformate prior to the addition of two moles of acrylonitrile. Hydrolysis of nitriles provides the phosphinic acid form of (V).

The phosphorus-containing diamine-dicarboxylic acid salts may also be formed by the reaction of a phosphorus-containing diamine salt of the formula

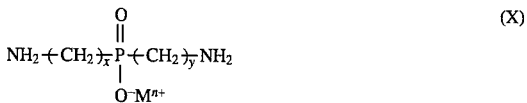 (X)

where x and y each are 2 or 3 and $M^{n+}$ is defined above with a dicarboxylic acid of the formula

 (XI)

wherein $R_3$ represents a hydrocarbon radical having from 4 to 12 carbon atoms, for example, polymethylene (e.g., tetramethylene or octamethylene), metaphenylene, paraphenylene, or the like.

The phosphorus-containing diamine salt (X) may be formed by reduction of $HP(CH_2CH_2CN)_2$ to $HP(CH_2CH_2CH_2NH_2)_2$ with subsequent oxidation at phosphorus, while the dicarboxylic acid (XI) is commercially available from Aldrich Chemical, Inc.

The phosphorus-containing metal salt may also be formed by reacting a phosphorus-containing diamine of formula (X) with a phosphorus-containing dicarboxylic acid of the formula (V).

As stated above, the polymer of the present invention is preferably formed by conventional melt polymerization in which an aqueous solution of at least one diamine-carboxylic acid salt is heated to remove water and effect polymerization. This solution is preferably a mixture which includes at least one conventional, non-phosphorus-containing, polyamide-forming salt in combination with the above P-containing salts in an amount sufficient to produce a polyamide. Preferably, the polyamide contains about 0.1% to 5.0% by weight phosphorus, most preferably 0.1% to 1.0% by weight phosphorus, based on the total weight of the polymer. Conventional polyamide salts are formed by reaction of diamines (VI) with dicarboxylic acids (XI) with the resulting salt providing the monomeric unit:

 (XII)

wherein $R_1$ and $R_2$ each is a radical selected from the group consisting of poll/methylene, having 4 to 12 carbon atoms, metaphenylene and paraphenylene. A preferred polyamide-forming salt is hexamethylenediamine adipate (nylon 6,6 salt) formed by the reaction of equimolar amounts of hexamethylenediamine and adipic acid and which supplies the monomeric unit

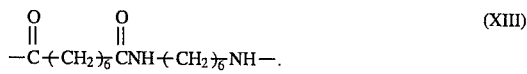 (XIII)

Other examples of salts which may be used to produce the polymers of this invention will be apparent to those skilled in the art. If desired, the reactant or reactants may contain one or more substituents which are unreactive under conditions employed to prepare the copolyamides. Such substituents will also be apparent to those skilled in the art.

The polymer of the present invention is particularly useful in forming fibers, particularly stain resistant fibers. Fibers of the present invention include a polymer having as an integral part of its polymer chain amide groups of the formula

and phosphinic acid-salt groups of the formula

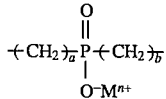

wherein both a and b are greater than or equal to 2 and $M^{n+}$ is selected from the group consisting of a monovalent (n=1) or divalent (n=2) cations.

Preferably, the polymer used in the fiber of the present invention contains from about 0.1% to 5.0% phosphorus, most preferably from about 0.1% to 1.0% phosphorus, by weight based on the total weight of the polymer. Most preferably, the polymer is a polyamide, i.e., the amide groups are linkages between repeat units in the polymer.

The fibers of the present invention may be manufactured by methods well known in the art. Preferably, the fibers are formed by conventional melt spinning techniques wherein a molten polymer is extruded through capillaries in a spinneret to form fibers as the polymer solidifies. The fiber may also be formed by conventional wet or dry solution spinning techniques wherein a solution of polymer is extruded through capillaries in a spinneret into a coagulation bath (wet spinning) or an evaporative environment (dry spinning).

The cross section and denier of the fibers of the present invention may vary greatly depending on the particular end use desired. The fiber cross section may be any cross section known in the art including, for example, round, trilobal, multifoliate, and the like. Preferred fibers of the present invention include the polymer of the present invention as their sole polymeric component; however, it is to be understood that the fibers of the present invention may include a blend of the polymer of the present invention with one or more other polymers, including, for example, polyamides or polyesters. Further, the fibers of the present invention may be bicomponent fibers, for example, conventional sheath/core and "racing stripe" fibers, which include discrete portions of the polymer of the present invention and discrete portions of another polymer.

In a first preferred embodiment, the fiber of the present invention is a pigmented fiber, defined as a fiber to which color has been imparted via a material added to the polymer which is substantially nonreactive therewith.

In a second preferred embodiment, the fiber of the present invention is a "dyed" fiber, defined as a fiber to which color has been imparted via a material which reacts with the polymer in the fiber. Preferred dyes are basic dyes.

The following example, while not intended to be limiting, illustrates a process for producing the polymer of the present invention as well as the fiber of the present invention.

EXAMPLE 1

A. Synthesis of Bis(2-carboxyethyl)phosphinic acid

This comonomer was prepared by the oxidation and subsequent hydrolysis of $HP(CH_2CH_2CN)_2$. To 20 g (0.1428 mol) of $HP(CH_2CH_2CN)_2$ [Strem Chemicals, Inc. product] is added 50 ml glacial acetic acid with stirring. Drop-wise to this solution is added 35 g hydrogen peroxide (30%) at slow speed to avoid violent reaction and keep reaction temperature below 40° C. After addition of the hydrogen peroxide, the solution temperature is held at 50° C. for two more hours. After allowing the reaction mixture to stand overnight at room temperature, the solution is evaporated to dryness in vacuo. The remaining solid melts from 69°–75° C. This material [ i.e., $HOPO (CH_2CH_2CN)_2$] was dissolved in 23ml methanol with stirring. To this mixture is added 23 g (0.575) NaOH in 23ml $H_2O$ and the solution is refluxed until evolution of ammonia ceases (about 2 hours). The 10 solution is then refluxed 2 more hours and evaporated to dryness in vacuo. Extraction of the solids was made with hot glacial acetic acid which after cooling was crystallized by adding small amounts of acetone yielding 20.4 g (68%) product. Recrystallization from acetic acid/acetone twice gave product used for polymerization {top 152°–157° C., literature mp 156°–159° C. [JOC 26 4628 (1961)]}. IR patterns were consistent with IR patterns visible in a compound of known structure, i.e., $PhPO(OH)CH_2COOH$. NMR analysis confirmed the structure. Titration with NaOH revealed one strong acid group (POOH) and two weaker carboxyl acids confirming a theoretical molecular weight of 210.15 for bis(2-carboxyethyl)phosphinic acid.

B. Polymer Preparation

To a stirred laboratory size autoclave is added 232 g nylon 6,6 salt (50% solution) and a solution of 3.4243 g (0.0163 mol) bis (2-carboxyethyl)phosphinic acid, 0.6518 g NaOH (0.0163 mol) and 3.7800 g (0.0163 mol) hexamethylene diamine (50% solution). Autoclave temperature is increased to 143° C. (20 psi) which concentrates the salt solution to 78–80%. Pressure is increased to 250 psi. The melt temperature is allowed to increase to 243° C. (250 psi). In the next 55 minutes, the temperature is increased to 285° C. as pressure is reduced to atmospheric pressure. The resulting polymer melt is then allowed to equilibrate for a 20-minute hold cycle.

C. Fiber Spinning

The molten equilibrated polymer was melt-spun directly from the bottom of the autoclave through a 6-hole spinneret. A portion of the yarn was left in as-spun conditions while the remaining yarn was dram to approximately 46.0 denier (15–24% elongation).

X-ray analysis of the resulting spun yarn indicated a phosphorus content in the polymer of 0.49% with a polymer relative viscosity of 37.

EXAMPLE 2

The synthesis of bis(2-carboxyethyl)phosphinic acid was repeated as in Example 1. A polymer was prepared as in Example 1 except a solution of 3.0 g bis(2-carboxyethyl)phosphinic acid, 0.580 g NaOH and 2.7 g hexamethylenediamine were mixed to form a copolymer having a theoretical phosphorus content of 0.45% by weight. Fiber produced by the process of Example 1 was found by x-ray analysis to have a phosphorus content of 0.42% by weight.

EXAMPLE 3

Phosphinic acid of the formula (IX) was also prepared from hypophosphorus acid as follows: Water was first removed from commercially available hypophosphorus acid (50% solids) at 50° C. under 0.05 mm vacuum using liquid nitrogen to trap water vapors. Caution: The heating bath must not go higher than 50° C. because this can cause decomposition of $H_2PO_2H$ to phosphine which is extremely reactive if air is vented to the system. At all times, $N_2$ gas should be used to release vacuum. There is no danger of phosphine formation however, if the heating bath stays at 50° C. or lower.

The final substance, i.e., $H_2PO_2H$, invariably contains 4–5% water, but this moisture level does not interfere with subsequent reactions. This near dry hypophosphorous acid crystallizes if held at 20° C. 1.1 moles of trimethyl orthoformate is added to this solid product under $N_2$ following a known literature procedure as disclosed by S. Fitch (JACS 86 61 [1964]), the disclosure of which is incorporated herein by reference. This mixture is worked up by evaporation of the solution at room temperature and is used in this crude form for the next step.

To this crude phosphorus-ester product at 1°–3° C. is added 3.3 moles of acrylonitrile (and 0.3 moles of triethylamine catalyst) according to a procedure published by M. J. Gallagher and J. Sussman (Phosphorus 5 91 [1975]), the disclosure of which is incorporated herein by reference. In addition to the reaction time reported in the paper, the reaction mixture was heated two additional hours to secure the addition of two moles of acrylonitrile.

The dinitrile product was converted to the phosphinic acid (IX) by hydrolysis in concentrated HCl (1–2 mole excess) at 90° C. for 3 hours. On cooling, the acidic solution was filtered to remove $NH_4Cl$. Concentration of the solution further resulted in additional $NH_4Cl$ which was filtered while the solution was hot. After all the water was removed, the heavy oil was extracted with 90° C. acetic acid and filtered hot. On cooling this final acetic acid solution, dicarbethoxy-phosphinic acid (IX) crystallized. Recrystallization of this crude product from acetic acid/acetone gave (IX), mp 150°–155° C., which was undepressed when mixed with product from $HP(CH_2CH_2CN)_2$ described in Examples 1 and 2 above.

Polymer and fiber were prepared with this comonomeric phosphinic acid salt (from $H_2PO_2H$) using polymerization and spinning processes described for Examples 1 and 2. Polymer RV was 40, and the yarn utilized for stain tests below contained 0.33% by weight phosphorus.

EXAMPLE 4

A. In this example, 2.21g bis (2-carboxyethyl)phosphinic acid was neutralized with 1-equivalent potassium hydroxide prior to addition of 1-equivalent of hexamethylenediamine. This final salt mixture in water (50%) was polymerized with 150g (75%) nylon 6,6 salt and spun into fiber as described in Example 1. The as spun fiber (RV 43.5) contained 2500 ppm phosphorus.

B. In this example, 2.21g bis(2-carboxyethyl)phosphinic acid was neutralized with ½-equivalent of magnesium hydroxide prior to the addition of 1-equivalent of hexamethylenediamine. This phosphorus tri-salt solution (50% water) was mixed with 150 g nylon 6,6 salt solution (75%) and polymerized/spun from a 130 g autoclave as described in Example 1. This yarn (RV 39.3) contained 2500 phosphorus.

EXAMPLE 5

A control sample of nylon 6,6 was prepared in the same autoclave as Examples 1–3 by polymerizing 300g of hexamethylenediamine adipate (50% solution) under the same process conditions as Examples 1, 2 and 3. This polymer was extruded into fibers as in the previous examples to provide control fiber samples for testing.

The following tests were conducted to compare the fibers produced in Examples 1–3 and 5.

A. Tenacity

The undrawn fibers of Example 1 were tested for spun tenacity using a conventional industrial model instrom instrument. Spun fibers produced in accordance with Example 1 were also drawn 3.2–3.5 times in the conventional manner and tested for tenacity with the same instrument.

Spun Example 1 fibers exhibited a tenacity of 1.22 g/denier while dram Example 1 fibers exhibited a tenacity of 7.8 g/denier. This may be compared to nylon 6,6 yarn which, when spun and dram under similar conditions, has a spun yarn tenacity of 1.0 to 1.2 g/denier and a drawn yarn tenacity of 4.5 to 7.0 g/denier.

B. Phosphorus Stability

To determine if the phosphorus is chemically bonded within the polymer chain, the fiber from Example 2 (by analysis: Phos 0.42%) was boiled in water containing ammonium sulfate at a solution pH of 4.5 for 60 minutes. This fiber, after rinsing and drying, was again checked for yarn phosphorus which was 0.41% by x-ray analysis. This test confirms that the phosphorus is bonded as an integral part of the polymer chain.

C. Yarn Luster and Whiteness

To determine yarn luster, a scale of 1–5 is used for visual assessment with more luster being present at the lower numbers. For example, the control yarn of Example 3 provides a 3-luster value. The phosphorus test yarn of Example 2 was given a 2-luster when a visual comparison was made with this control yarn. With whiteness, a 1–5 scale is also used with a 1-value representing a yarn colorless and very near pure white. Control nylon yarns spun under conditions described above, i.e., from the small laboratory autoclave, generally exhibit whiteness values of 1–2 and this same 1–2 value for whiteness was given to the test yarn of Examples 1 and 2.

D. Stain Resistance

Test yarns containing 0.33% phosphorus (Example 3) and 0.45% phosphorus (Example 2) in drawn form were exposed to a Kool-Aid solution (20 ml of 10% solids) for a two-minute soak. Fiber was removed and allowed to remain on a watch glass for eight hours, then rinsed and fiber color (shade of pink) compared to control fiber of Example 5 which had undergone identical Kool-Aid contact. A rating scale of 1–8 is used to identify the degree of staining of the sample as measured visually with 1 being equal to deep red and 8 being equal to white (no stain), and with a fiber being classified as "stain resistant" if it achieves a rating of 6, 7 or 8. The test yarn (Example 3) achieved a 7-rating and Example 2 test yarn achieved an 8-rating while the control yarn was assigned a value of 1.

E. Flammability

The flame resistant properties of the yarn of both Examples 1 and 2 were tested separately by a procedure (Ref. Tex. Res. J. 45 474 [1975]) in which three 18-inch long yarn samples, prepared by combining 50 strands of the target yarn, i.e., either Example 1 or Example 2 yarn, are burned in the vertical position. Initially, the yarn bundle is ignited at the bottom of the bundle. After ignition, the yarn bundle would burn upward for a short time and then go out. The yarn bundle would be reignited and allowed to burn until it self-extinguished again. This process is repeated until the entire sample is consumed. The more reignition times required for complete yarn consumption, the more flame resistant the yarn. Each burn value is an average of 3-trials. Example 1 yarn exhibited a burn value of 27, Example 2, 26. In similar fashion, three 50-strand samples prepared from the control yarn of Example 5 were also tested. This yarn sample required less ignitions, i.e., 16–17 ignitions, illustrating that the yarns of the present invention are more flame resistant than the nylon control yarns.

As is clearly shown from the data above, fibers formed from the polyamide copolymer of the present invention exhibit tenacity, luster, and whiteness characteristics equal to that of nylon 6,6 fibers while demonstrating stain resist properties far superior to that of nylon 6,6 in addition to enhanced flame resistance. The copolymer and the fibers formed therefrom are therefore highly useful in carpet manufacture.

Although the present invention has been described herein with detail and with reference to preferred embodiments, it is to be understood that variations in the present invention may be made without departing from the spirit and scope thereof. For example, the polyamide copolymer of the present invention maybe colored in a solution-dye process utilizing color pigments (including $TiO_2$) which are stable to molten nylon temperatures, or may be basic dyed. The copolymer of the present invention may also be blended with various conventional additives typically utilized in fiber-making processes including antioxidants, heat stabilizers, optical brighteners and fillers.

I claim:

1. A fiber comprising a synthetic polymer, said polymer including as integral parts of its polymer chain amide groups of the formula

and phosphinic acid-salt groups of the formula

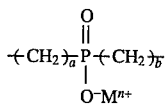

wherein a and b are beth greater-than or equal to 2 and wherein $M^{n+}$ is selected from the group consisting of monovalent (n=1) and divalent (n-2) cations.

2. The fiber of claim 1 wherein said phosphinic acid-salt groups are present in an amount sufficient to provide 0.1% to 5% by weight phosphorus based on the total weight of said polymer.

3. The fiber of claim 1 wherein said polymer is polyamide and includes repeat units of the formula

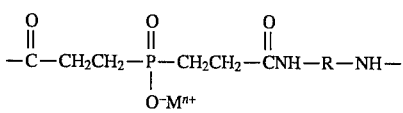

wherein R represents an alkyl having 4 to 12 carbon atoms.

4. The fiber of claim 3 wherein said phosphinic acid-salt groups are present in an amount sufficient to provide 0.1% to 5% by weight phosphorus based on the total weight of said polymer.

5. The fiber of claim 1 wherein said polymer is a polyamide and includes repeat units of the formula

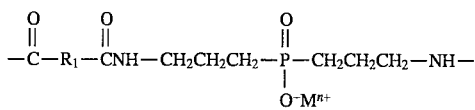

wherein $R_1$ represents an alkyl having 4 to 12 carbon atoms.

6. The fiber of claim 5 wherein said phosphinic acid-salt groups are present in an amount sufficient to provide 0.1% to 5% by Weight phosphorus based on the total weight of said polymer.

7. The fiber of claim 1 wherein said polymer is a polyamide and includes repeat units of the formula

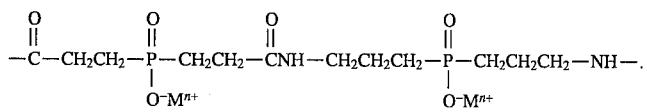

8. The fiber of claim 7 wherein said phosphinic acid-salt groups are present in an amount sufficient to provide 0.1% to 5% by weight phosphorus based on the total weight of said polymer.

9. The fiber of claim 1 wherein said polymer is a polyamide and includes repeat units of the formula

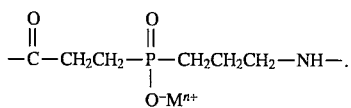

10. The fiber of claim 9 wherein said phosphinic acid-salt groups are present in an amount sufficient to provide 0.1% to 5% by weight phosphorus based on the total weight of said polymer.

11. A synthetic polymer including as integral parts of its polymer chain (1) amide groups of the formula

and phosphinic acid-salt groups of the formula

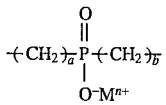

wherein a and b are both greater than or equal to 2 and wherein M is selected from the group of cations where n=1 or 2.

12. The polymer of claim 11 wherein said phosphinic acid-salt groups are present in an amount sufficient to provide 0,1% to 5% by weight phosphorus based on the total weight of said polymer.

13. The polymer of claim 11 wherein said polymer is a polyamide and includes repeat units of the formula

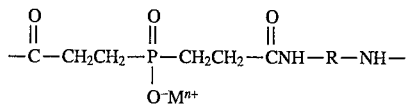

wherein R represents an alkyl having 4 to 12 carbon atoms.

14. The polymer of claim 13 wherein said phosphinic acid-salt groups are present in an amount sufficient to provide 0.1% to 5% by weight phosphorus based on the total weight of said polymer.

15. The polymer of claim 11 wherein said polymer is a polyamide and includes repeat units of the formula

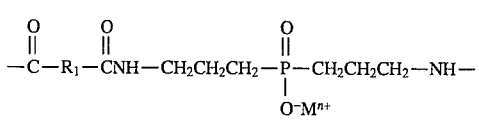

wherein $R_1$ represents an alkyl having 4 to 12 carbon atoms.

16. The polymer of claim 15 wherein said phosphinic acid-salt groups are present in an amount sufficient to provide 0.1% to 5% by weight phosphorus based on the total weight of said polymer.

17. The polymer of claim 11 wherein said polymer is a polyamide and includes repeat units of the formula

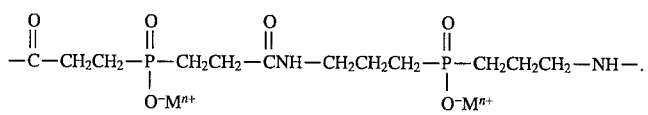

18. The polymer of claim 17 wherein said phosphinic acid-salt groups are present in an amount sufficient to provide 0.1% to 5% by weight phosphorus based on the total weight of said polymer.

19. The polymer of claim 11 wherein said polymer is a polyamide and includes repeat units of the formula
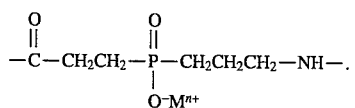
20. The polymer of claim 19 wherein said phosphinic acid-salt groups are present in an amount sufficient to provide 0.1% to 5% by weight phosphorus based on the total weight of said polymer.
* * * * *

UNITED STATES PATENT AND TRADEMARK OFFICE
CERTIFICATE OF CORRECTION

PATENT NO.  : 5,545,833
DATED       : Aug. 13, 1996
INVENTOR(S) : John W. Stoddard It is certified that error appears in the above-indentified patent and that said Letters Patent is hereby corrected as shown below:

Column 2, line 21, --radicals.-- should be inserted before "Also, U.S."

Column 5, line 67, "poll/methylene" should be spelled --polymethylene--

Column 7, line 27, "top" should be --mp--

Column 9, lines 15 and 17, "dram" should be spelled --drawn-- in each occurence.

Column 10, line 48, "beth greater-than" should read --both greater than--

Column 10, line 50, "(n-2)" should be --(n=2)--

Column 12, line 1, "0,1%" should be --0.1%--

Signed and Sealed this

Eleventh Day of February, 1997

Attest:

BRUCE LEHMAN

Attesting Officer

Commissioner of Patents and Trademarks